United States Patent
Fleischer et al.

(12)

(10) Patent No.: US 6,235,243 B1
(45) Date of Patent: May 22, 2001

(54) GAS SENSOR ARRAY FOR DETECTING INDIVIDUAL GAS CONSTITUENTS IN A GAS MIXTURE

(75) Inventors: Maximilian Fleischer, Munich; Hans Meixner, Haar, both of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 07/928,443

(22) Filed: Aug. 12, 1992

(30) Foreign Application Priority Data

Aug. 14, 1991 (EP) .................................................. 91113661

(51) Int. Cl.[7] .......................... G01N 31/12; G01N 27/00; G01N 25/00; H01N 6/30
(52) U.S. Cl. ............................. 422/94; 422/98; 73/25.05; 73/31.05; 73/31.06; 429/111
(58) Field of Search ................................ 73/25.05, 31.05, 73/31.06; 422/94, 98; 429/111

(56) References Cited

U.S. PATENT DOCUMENTS

| Re. 33,980 | * | 6/1992 | Matsuura et al. | 422/98 |
|---|---|---|---|---|
| 4,045,729 | * | 8/1977 | Loh | 422/98 |
| 4,057,996 | * | 11/1977 | Firth et al. | 73/31.05 |
| 4,347,732 | * | 9/1982 | Leary | 73/31.05 |
| 4,453,397 | * | 6/1984 | Ohta et al. | 73/31.05 |
| 4,457,161 | | 7/1984 | Iwanaga et al. | 73/31.05 |
| 4,533,608 | * | 8/1985 | Somorjai et al. | 429/111 |
| 4,542,640 | * | 9/1985 | Clifford | 73/31.05 |
| 4,574,264 | | 3/1986 | Takahashi et al. | 73/31.06 |
| 4,584,867 | * | 4/1986 | Forster | 73/31.05 |
| 4,792,433 | * | 12/1988 | Katsura et al. | 422/98 |
| 4,991,424 | * | 2/1991 | Lehto | 73/25.05 |

FOREIGN PATENT DOCUMENTS

| 0 141 090 | 5/1985 | (EP) . |
|---|---|---|
| 2 331 016 | 6/1977 | (FR) . |
| 1 527 406 | 10/1978 | (GB) . |
| 1 562 623 | 3/1980 | (GB) . |

OTHER PUBLICATIONS

Morrison, "Chemical Sensing with Solid State Devices", Academic Press, Inc. 1989, pp. 520–523.

Michel:, Adolph L., et al., Ceramic Engineering Science Proceedings, 8[9–10] pp. 1095–1105, (1987).*

* cited by examiner

Primary Examiner—Lynette R. F. Smith
(74) Attorney, Agent, or Firm—Schiff Hardin & Waite

(57) ABSTRACT

A gas sensor array for detecting individual gas constituents in a gas sensor, said array being composed of a carrier member of a non-conductive substrate having a plurality of individual sensor elements formed by semiconductor oxides being applied thereon in a planar arrangement and the array is provided with contact electrode arrangements for measuring electrical conductivity, with a heating arrangement for heating a predetermined operating temperature and with protective sheaths for protecting the arrangement against external influences along with a fastening base so that the individual operating temperatures allocated to the various sensors and wherein the differences between respective sensor signals are formed for detecting the individual gas constituents, with these differences being supplied to a processing unit. In a preferred embodiment, at least one part of the individual sensor element is composed of a $\beta$-$Ga_2O_3$ thin film.

33 Claims, 5 Drawing Sheets

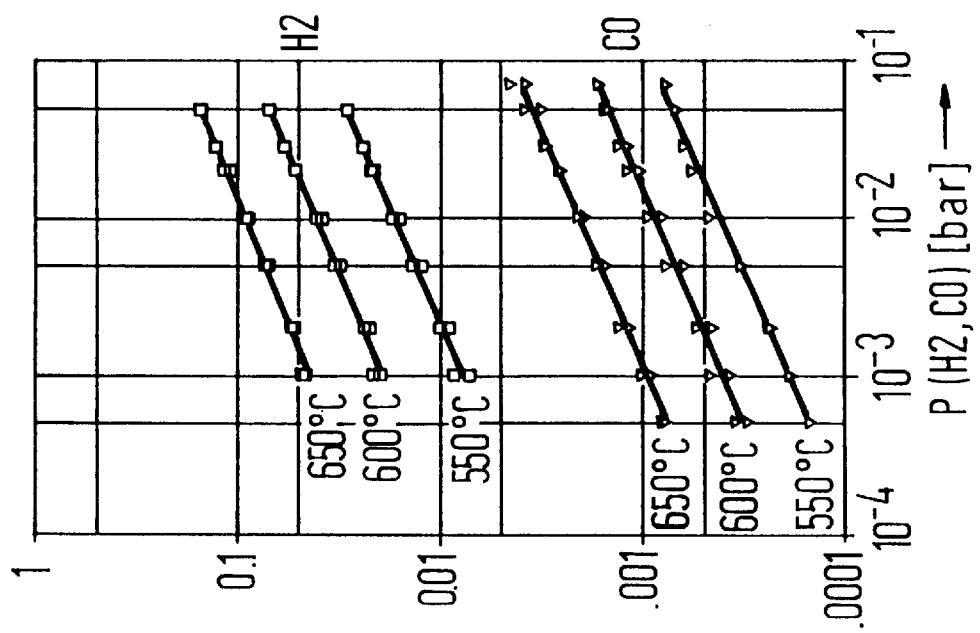
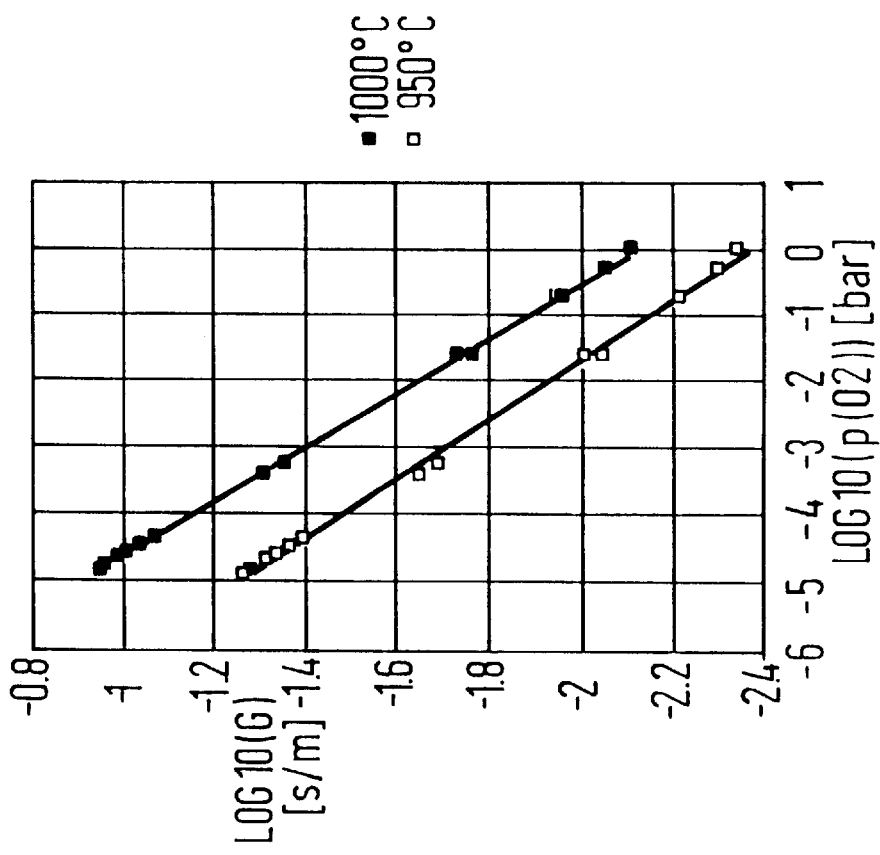

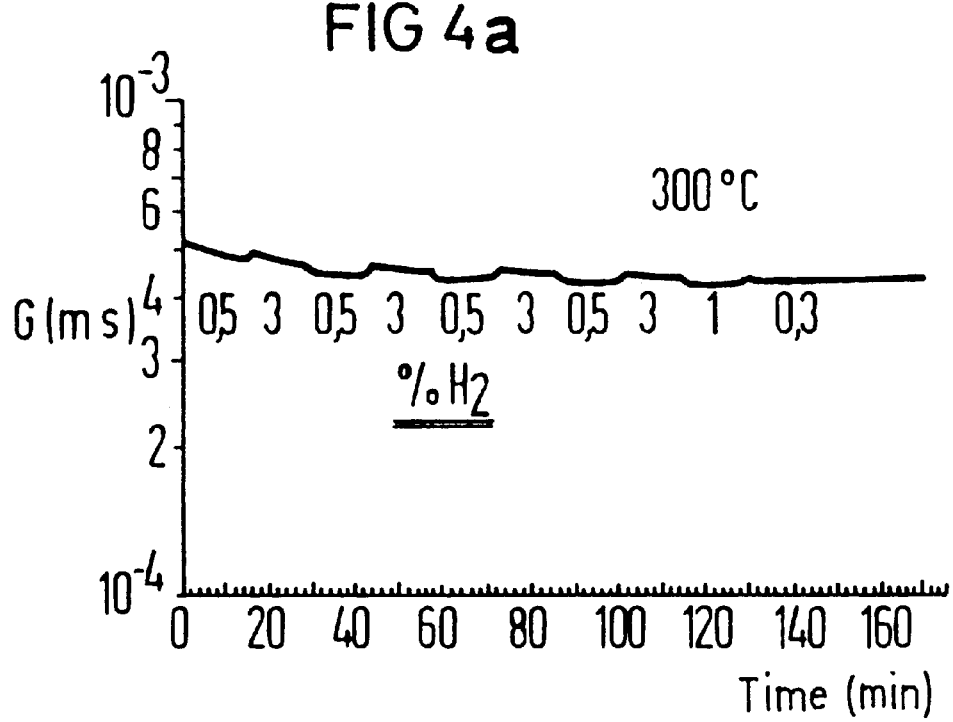
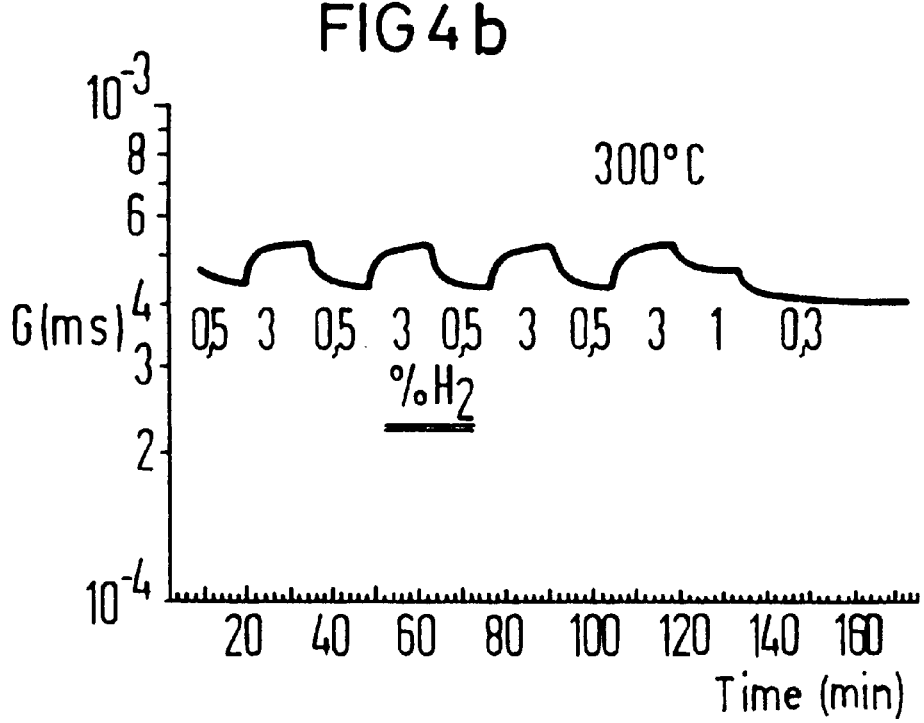

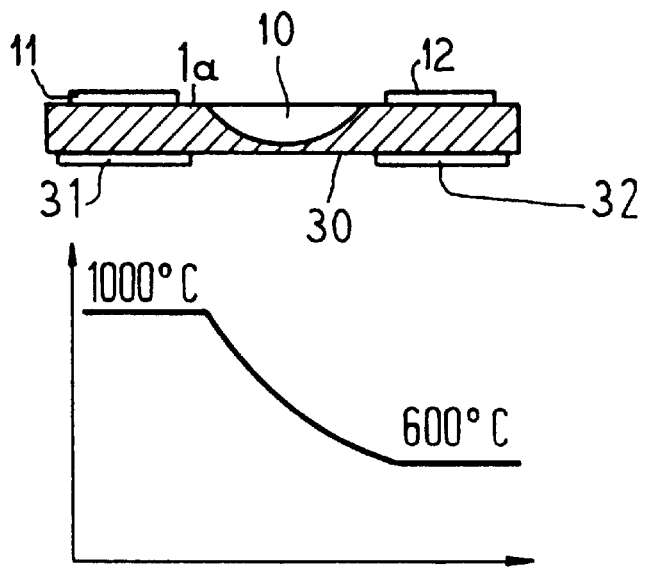
FIG 5a
FIG 5b
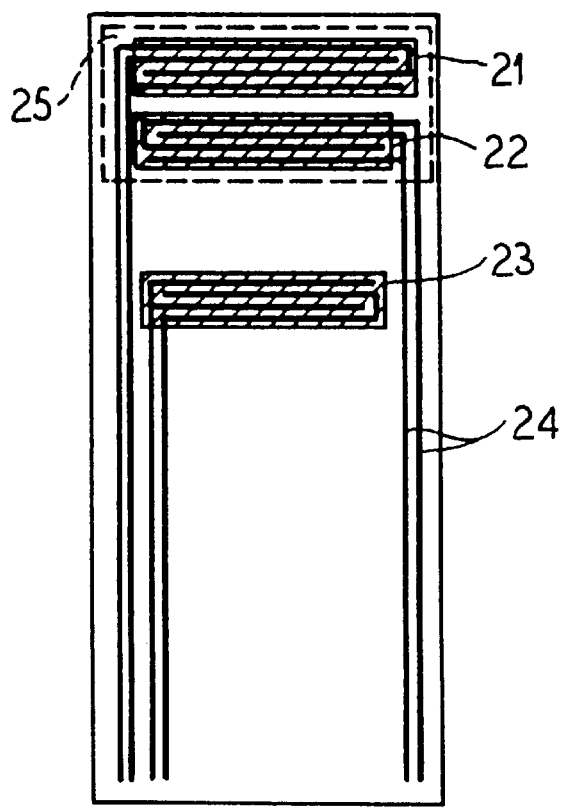
FIG 6

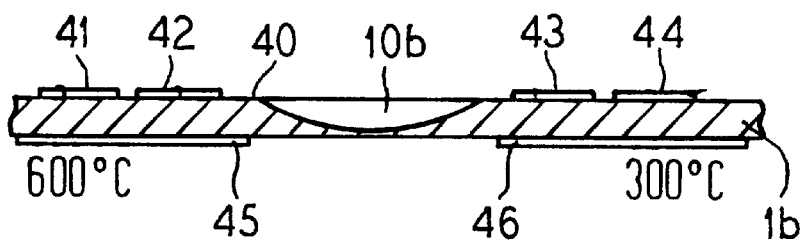
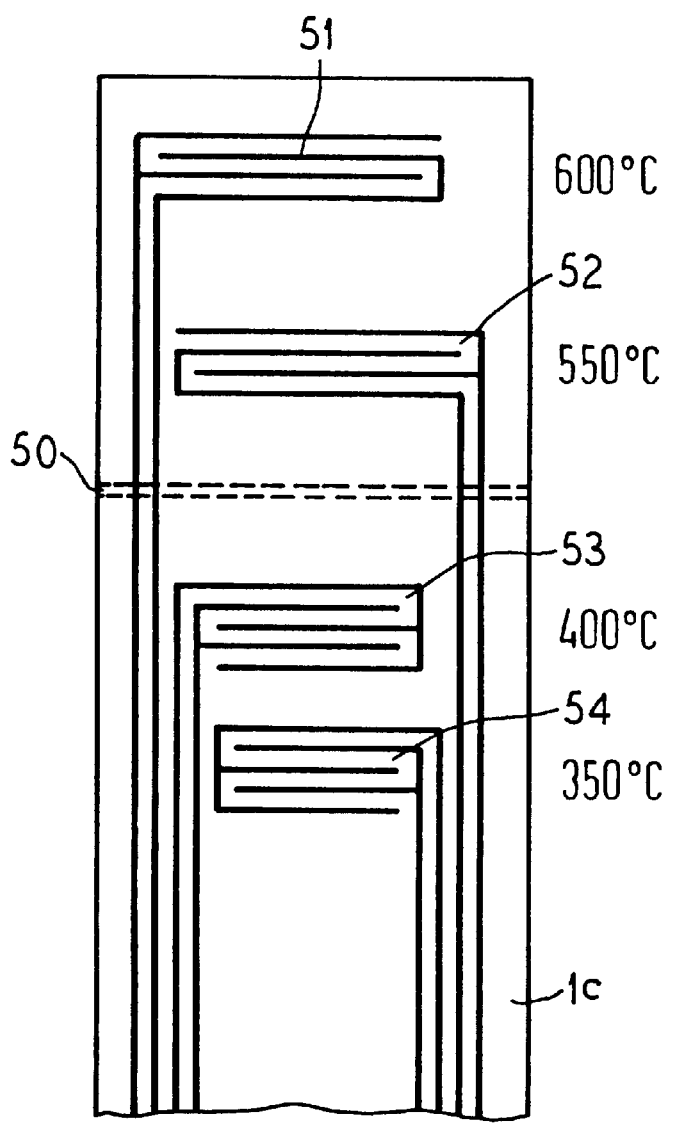

GAS SENSOR ARRAY FOR DETECTING INDIVIDUAL GAS CONSTITUENTS IN A GAS MIXTURE

BACKGROUND OF THE INVENTION

The present invention is directed to a gas sensor array for detecting individual gas constituents in a gas mixture. The array is composed of a plurality of individual sensor elements, which include semiconductive oxides, wherein the individual sensor elements are respectively applied on an electrically non-conductive substrate and wherein the array is provided with a contact electrode arrangement for measuring the electrical conductivity. In addition, the array includes a heating arrangement for heating to a given predetermined operational temperature, a protective sheath, which will protect the array against external mechanical influences, and a fastening base are also provided. The individual sensor elements have prescribed, individual operating temperatures allocated to them and the combinations between the respective sensor signals are formed for detecting the individual gas constituents, and these combinations are supplied to a processing unit.

Two proposals have been disclosed for selectively detecting and quantifying individual constituents in a gas mixture of chemically different gases. One of these proposals is directed to what is referred to as analysis equipment, wherein, for example, the employment are provided for quadripole mass spectroscopy or "FTIR". These relatively involved apparatus have the required suitability for measuring jobs at testing stands, such as, for example, motor testing stands and gas measuring stations. In the field of what is referred to as a low-cost apparatus that can be employed for monitoring jobs, it has also been proposed to employ gas sensors on the basis of heated tubes of semiconductive $SiO_2$, which is provided with different precious metal dopings in order to obtain the selectivity of the sensor for a specific gas by projection. See, for example, an article by J. Watson and A. Price, *Proc. IEEE*, Vol. 66, 1978, p. 1670, which article is directed to an investigation of the selectivity of such sensors with respect to CO and to $CH_4$.

These latter sensors have high transverse sensitivities, for example they are generally sensitive not only for the gas to be detected but also other gases. Given such sensors for reducing gases on the basis of $SnO_2$, for example, the sensor with the basic material $SnO_2$ is also $O_2$-sensitive, for example, these sensors for reducing gases also react to $O_2$. Evaluation methods based on the principle of a pattern recognition can only be conditionally implemented with these sensors, since the individual sensors of an appertaining array do not generally comprise the stability required for this purpose. The problems that occur are based on the drift of the sensor signal and on unit scatter. In this respect, see a portion of a book by S. R. Morrison, *Chemical Sensing with Solid State Devices*, Academic Press, New York, 1989, Chapter 13.1.2.

Similarly constituted problems also occur given other standard sensor materials, such as, for example, $Fe_2O_3$, $TiO_2$ and, in particular, ZnO.

SUMMARY OF THE INVENTION

An object of the present invention is to create a gas sensor array for detecting individual gas constituents in a gas mixture that, with high reliability and low transverse sensitivity, enables detecting and quantifying of the individual constituents in the gas mixture of chemically different gases, and the gas sensor array should have a cost-beneficial structure.

These objects are obtained in an improvement in a gas sensor array for detecting individual gas constituents in a gas mixture, said array being composed of a plurality of individual sensor elements which are based on semiconductor metal oxides, said sensor elements being respectively applied on electrically non-conductive substrates, the array being provided with a contact electrode arrangement for measuring the electrical conductivity and being provided with a heating arrangement for heating at a predetermined operating temperature, with a protective sheath that protects the array against external mechanical influences and with a fastening base wherein the individual sensor elements have prescribed individual operating temperatures allocated to them and wherein differences between respective sensor signals are formed for detecting individual gas constituents, with these differences being supplied to a processing unit. The improvements are that at least one part of the individual sensor element is based on a $\beta$-$Ga_2O_3$ thin film and that all individual sensor elements are provided on a common substrate in a planar arrangement.

The invention allows the employment of arrays that contain individual sensor elements on the basis of catalytically non-active, stable semiconductive thin layers or films, for example $Ga_2O_3$, wherein, in the case of the individual sensor elements, the following is present:

a selection between oxygen sensitivity and sensitivity for reducing gases is made by selecting the operating temperature;

individual sensor elements are lent a specific sensitivity for individual, non-reducing gases on the basis of designational, catalytic activation of the $Ga_2O_3$, which, itself, is not catalytically active and by selecting a suitable operating temperature; and a setting of the sensitivity for oxidizing gases ($NO_x$, $Cl_2$ and $Br_2$) is possible by varying the type of semiconduction by doping the material (for example changing to a p-type).

Other advantages and features of the invention will be readily apparent from the following description of the preferred embodiments, the drawings and claims.

BRIEF DESCRIPTION OF THE DRAWINGS

FIG. 1b is an enlarged cross sectional view of a portion of the sensor element of FIG. 1a;

FIG. 2 is a graph showing the sensor characteristics of a $Ga_2O_3$ thin film oxygen sensor element for $O_2$ at different operating temperatures;

FIG. 3 is a graph showing the sensor characteristics of a $Ga_2O_3$ gas sensor element for detecting $H_2$ and CO at different operating temperatures;

FIGS. 4a and 4b are graphs illustrating the effects of catalytic activation of the $Ga_2O_3$ gas sensor;

FIG. 5a is a cross sectional view of a sensor arrangement for distinguishing between $O_2$ and a reducing gas with FIG. 5b showing a typical temperature curve relationship for the sensor arrangement;

FIG. 6 is a plan view of another exemplary embodiment for achieving different temperature ranges in a gas sensor array;

FIG. 7 is a schematic cross sectional view of a gas sensor array for the quantitative detection of individual gas constituents; and FIG. 8 is a partial plan view of an exemplary embodiment for achieving different temperature ranges in a gas sensor array.

DESCRIPTION OF THE PREFERRED EMBODIMENTS

Figure 1A:
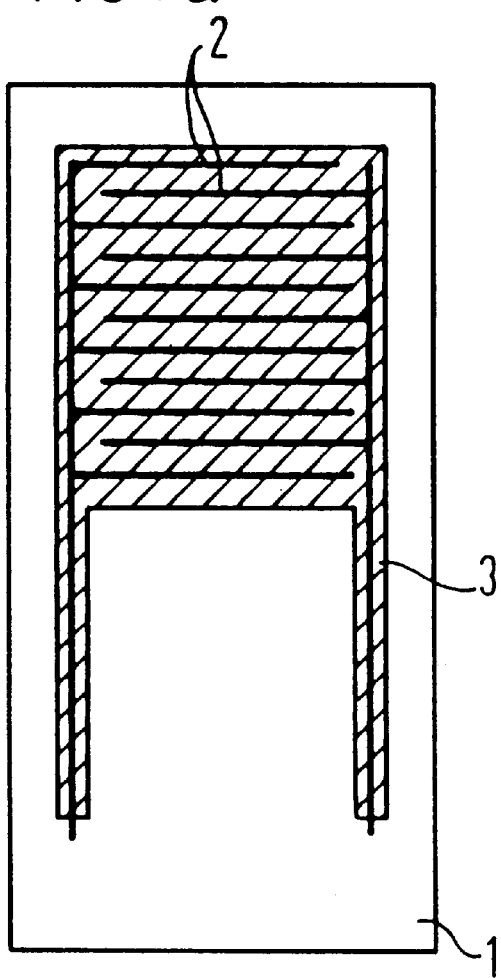
FIG. 1a is a plan view of a structure of an individual sensor element of the type that can be employed in a gas sensor array of the present invention.
Figure 1B:
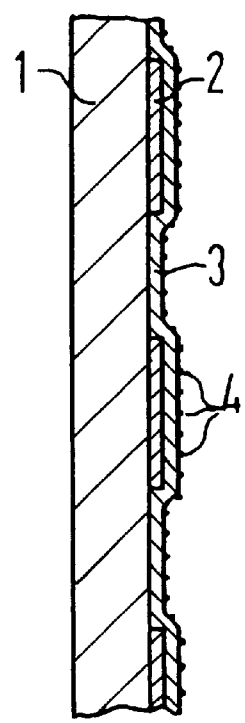

The principles of the present invention are particularly useful when incorporated in a gas sensor array for detecting individual gas constituents in a gas mixture which is composed of a plurality of individual sensor elements utilizing the basis of semiconductor metal oxides and wherein the individual sensor elements are respectively applied on an electrically non-conductive substrate 1 of FIGS. 1a and 1b. The array is provided with a contact electrode arrangement 2 for measuring the electrical conductivity, which arrangement may have the configuration of FIG. 1a. The array may have a heating arrangement for heating a predetermined operating temperature, as illustrated in FIG. 5a, with a protective sheath (not shown) that will protect the array against external mechanical influences and with a fastening base (not shown), wherein the individual sensor elements having a prescribed individual operating temperature allocated to them and wherein the combination of the respective sensor signals are formed for detecting the individual gas constituents, with these combinations of signals being supplied to a processing unit. Inventively, at least one of the individual sensor elements is based on $\beta$-$Ga_2O_3$ thin films 3 of FIG. 1a. All individual sensor elements are provided on a common substrate in a planar arrangement. At least one of the individual sensor elements is provided with at least one temperature-stable, finely dispersed, catalytically active material 4 (see FIG. 1b), whose effect is stable at the appertaining operating conditions that will prevail. The catalytically active material can be a precious metal or be an alloy having at least one precious metal. Pt, Pa, Rh or Ag can be expediently employed as the precious metal.

It is also inventively provided that the catalytically active material is a sub-group metal oxide. For example, sub-group metal oxides can be selected from a group consisting of $Nb_2O_3$, $Fe_2O_3$, $ZrO_2$ or $TiO_2$.

For manufacturing the gas sensor array of the invention, it is provided that the catalytically active material is applied onto a surface of the gas-sensitive $Ga_2O_3$ thin film in the form of a second layer or phase. The catalytically active material can also be doped or inserted into the gas-sensitive $Ga_2O_3$ thin film in the form of a second phase.

It is also provided that the originally n-semiconducting $Ga_2O_3$ thin film layer 3 may, in at least one of the individual sensor elements, be converted for acquisition for oxides and gases by being doped into a p-semiconducting thin film. The doping material is preferably MgO.

The individual sensor elements can have different layer morphologies or structures.

It is also inventively provided that the individual sensor elements differ in structure, dependent on the gas constituents to be acquired or dependent on the gas constituent group to be acquired. The operating temperatures can, therefore, be the same for the individual sensor elements. Over and above this, one exemplary embodiment provides that at least a part of the plurality of individual sensor elements has different operating temperatures allocated to them. These, however, can also have an identical structure, wherein different operating temperatures are allocated to the individual sensor elements.

The different operating temperatures are prescribed according to the gas constituents to be acquired or according to the gas sensor constituent group to be acquired, for example 950° C. for $O_2$ and 600° C. for reducing gases.

A heating structure is provided at the side of the carrier member facing away from the sensors. This heating structure, in cooperation with, essentially, the heat sink of the fastening base will produce a temperature gradient in the carrier member, and those regions where the individual sensor elements are arranged so that the different operating temperatures can be offered, as illustrated in FIG. 6, wherein sensor elements 21, 22 and 23 are disposed on the substrate, with each element having separate connecting lines, such as the line 24 for the element 22. The elements 21 and 22 are overlying an area 25, shown in broken lines, which has a temperature maximum.

According to one exemplary embodiment, regions of the carrier member that are essentially thermally isolated are provided on the basis of one or more heat barriers. Each of these regions has a separate heating structure allocated to it so that the different operating temperatures can be offered. Examples are shown in FIGS. 5a and 7.

In the embodiment of FIG. 5a, a substrate 1a is provided with a heat barrier 10, which is a depression or a Constriction in the substrate between a first sensor element 11 and a second sensor element 12. On a surface 30 of the substrate 1a opposite to the surface carrying the sensor elements 11 and 12, a heater 31 is provided under the element 11 and a heater 32 is provided under the element 12. As illustrated in FIG. 5b, due to the heat barrier 10 and the fact that the heaters 31 and 32 are independent of each other, the element 11 may be heated to 1000° C., while the element 12 is heated only to 600° C.

In the embodiment of FIG. 7, a substrate 1b has a heat barrier 10b formed on one surface 40 to separate two elements 41 and 42 from two other elements 43 and 44. The elements 41 and 42 overlie a heating structure 45, while the elements 43 and 44 overlie a heating structure 46. The heating structure 45 will heat the elements 41 and 42 to approximately 600° C., while the heating structure 46 heats only to a temperature of approximately 300° C. The element 41 is an n-type element for determining CO or $H_2$, while the element 42 is a p-type element for determining $NO_x$. The element 43 is an n-type+platinum element for determining $H_2$ and the element 44 is an n-type without platinum element for determining CO. In both the embodiments of FIGS. 5a and 6, the heating structures can be connected in series or in parallel, as desired. For example, the heating structure of FIG. 5a is illustrated as being connected in series but could be connected in parallel like the heating structure of FIG. 7.

A different operating temperature can be generated by the structure that occurs from a combination of the aforementioned arrangements. The heat barriers, for example, can be fashioned in the form of let-in portions or depression in the substrate or in a carrier member or in the form of a gap, such as a gap 50 formed in a substrate 1c of FIG. 8.

In the embodiment of FIG. 8, four sensor elements 51–54 are illustrated. These elements 51–54 are each operating at a descending temperature range, with the element 51 being in a range of 600° C. and the element 52 being at 550° C. and, on one side of the gap 50, while the third element 53 is at 400° C. and the fourth element is at 350° C. and are on the opposite side of the gap 50 from the first elements 51 and 52. The device may have a heat sink 60 cooperating with the gap 50 or with the heating structure.

For example, the carrier members can be composed of an aluminum free ceramic material or silica glass. However, it can also be provided that the carrier member is composed of silicon having at least one electrically insulating layer.

Although various minor modifications may be suggested by those versed in the art, it should be understood that we wish to embody within the scope of the patent granted hereon all such modifications as reasonably and properly come within the scope of our contribution to the art.

We claim:

1. In a gas sensor array for detecting individual gas constituents in a gas mixture, said array being composed of a plurality of individual sensor elements, which are the basis of semiconductive metal oxides, said individual sensor elements being respectively applied on an electrically non-conductive substrate, with the array being provided with a contact electrode arrangement for measuring the electrical conductivity of each element, the array being provided with a heating arrangement for heating at a predetermined operating temperature with a protective sheath that protects the array against external mechanical influences and a fastening base wherein the individual sensor elements have prescribed individual operating temperatures allocated to them and wherein differences between the respective sensor signals are formed for detecting the individual gas constituents, with these differences being supplied to a processing unit, the improvements comprising at least one of the individual sensor elements comprising a catalytically inactive $\beta$-$Ga_2O_3$ thin film being provided with a catalytically active material, and with all the individual sensor elements being provided on a common substrate in a planar arrangement.

2. In a gas sensor array according to claim 1, wherein the catalytically active material is a temperature-stable, finely dispersed, catalytically active material that is stable in terms of its effect at the appertaining operating conditions that prevail.

3. In a gas sensor array according to claim 2, wherein the catalytically active material is a precious metal.

4. In a gas sensor array according to claim 2, wherein the catalytically active material is an alloy having at least one precious metal.

5. In a gas sensor array according to claim 3, wherein the precious metal is Pt.

6. In a gas sensor array according to claim 3, wherein the precious metal is Pa.

7. In a gas sensor array according to claim 3, wherein the precious metal is Rh.

8. In a gas sensor array according to claim 3, wherein the precious metal is Ag.

9. In a gas sensor array according to claim 2, wherein the catalytically active material is a sub-group metal oxide.

10. In a gas sensor array according to claim 9, wherein the sub-group metal oxide is $Nb_2O_3$.

11. In a gas sensor array according to claim 9, wherein the sub-group metal oxide is $Fe_2O_3$.

12. In a gas sensor array according to claim 9, wherein the sub-group metal oxide is $ZrO_2$.

13. In a gas sensor array according to claim 9, wherein the sub-group metal oxide is $TiO_2$.

14. In a gas sensor array according to claim 2, wherein the catalytically active material is applied onto a surface of a gas-sensitive $Ga_2O_3$ thin film and is in the form of a second layer.

15. In a gas sensor array according to claim 2, wherein the catalytically active material is doped into the gas-sensitive $Ga_2O_3$ thin film and is in the form of a second phase.

16. In a gas sensor array according to claim 1, wherein an originally n-semiconducting $Ga_2O_3$ thin film of at least one of the individual sensor elements is converted by doping into a p-semiconducting thin film for acquiring oxidizing gases.

17. In a gas sensor array according to claim 16, wherein the doping material is MgO.

18. In a gas sensor array according to claim 1, wherein the individual sensor elements comprise different layer morphologies.

19. In a gas sensor array according to claim 1, wherein the individual sensor elements comprise different structures dependent on gas constituents to be detected and dependent on the gas constituent group to be detected.

20. In a gas sensor array according to claim 19, wherein the operating temperatures for the individual sensor elements are identical.

21. In a gas sensor array according to claim 19, wherein at least one part of the plurality of individual sensor elements has a different operating temperature allocated to them.

22. In a gas sensor array according to claim 1, wherein the individual sensor elements comprises individual structures and different operating temperatures are allocated to the individual sensor elements.

23. In a gas sensor array according to claim 22, wherein the different operating temperatures are selected and are dependent on the gas constituents to be detected and dependent on the gas sensor constituent groups to be detected with 950° C. being selected for $O_2$ and 600° C. for reducing gases.

24. In a gas sensor array according to claim 22, wherein heating structures are provided on a side of the substrate facing away from the sensor, said heating structure cooperating with a heat sink of a fastening base generating a temperature gradient in the substrate in a region of the individual sensor elements that are arranged so that different operating temperatures are offered.

25. In a gas sensor array according to claim 22, wherein regions of the substrate are essentially thermally insulated by a heat barrier being provided and that each of these regions have a separate heating structure allocated to it so that the different operating temperatures can be provided.

26. In a gas sensor array according to claim 25, wherein the heating structures are connected in series.

27. In a gas sensor array according to claim 25, wherein the heating structures are connected in parallel.

28. In a gas sensor array according to claim 22, wherein different operating temperatures are generated by a structure that includes a combination of a heat sink cooperating with a heating element and at least one heat barrier.

29. In a gas sensor array according to claim 22, wherein a heat barrier is provided and is in the form of a constricted portion on the substrate.

30. In a gas sensor array according to claim 22, wherein a heat barrier is provided and is in the form of a gap in the substrate.

31. In a gas sensor array according to claim 1, wherein the substrate is composed of aluminum-free ceramic material.

32. In a gas sensor array according to claim 1, wherein the substrate is composed of silica glass.

33. In a gas sensor array according to claim 1, wherein the substrate is composed of silicon having at least one electrically insulating layer.

* * * * *